(12) United States Patent
Kagawa et al.

(10) Patent No.: US 8,419,941 B2
(45) Date of Patent: Apr. 16, 2013

(54) ETHANOL WATER SOLUTION CONCENTRATING METHOD

(75) Inventors: Kazuhiro Kagawa, Wako (JP); Pu Qian, Wako (JP); Akihisa Tanaka, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 380 days.

(21) Appl. No.: 12/752,030

(22) Filed: Mar. 31, 2010

(65) Prior Publication Data
US 2010/0224560 A1 Sep. 9, 2010

(30) Foreign Application Priority Data
Apr. 3, 2009 (JP) ................................. 2009-091493

(51) Int. Cl.
*C02F 3/00* (2006.01)
*B01D 61/00* (2006.01)

(52) U.S. Cl.
USPC ........... 210/607; 210/649; 210/650; 210/651; 210/652; 210/653; 210/654; 210/655

(58) Field of Classification Search .................. 210/607, 210/649–655
See application file for complete search history.

(56) References Cited

U.S. PATENT DOCUMENTS
| | | |
|---|---|---|
| 5,096,586 A | 3/1992 | Kaner et al. |
| 6,899,743 B2 * | 5/2005 | Wijmans et al. .................. 95/50 |
| 7,819,944 B2 | 10/2010 | Yajima et al. |
| 2006/0117955 A1 * | 6/2006 | Cranford et al. .................. 96/14 |
| 2009/0215139 A1 * | 8/2009 | Datta et al. ..................... 435/162 |

FOREIGN PATENT DOCUMENTS
| | | |
|---|---|---|
| JP | 61-167405 A | 7/1986 |
| JP | 2006-136263 A | 1/2006 |
| JP | 2006-088136 A | 6/2006 |
| WO | 2007-119286 A1 | 10/2007 |

OTHER PUBLICATIONS

Ado, Yutaka, "Alcohol Production from Cellulosic Biomass," Journal of Wood Science, Oct. 23, 1989, vol. 35, No. 12, pp. 1067-1072, The Japan Wood Society.
English Abstract—Ado, Yutaka, "Alcohol Production from Cellulosic Biomass," Journal of Wood Science, Oct. 23, 1989, vol. 35, No. 12, pp. 1067-1072, The Japan Wood Society.
Zhou, M., Persin, M., and Sarrazin, J., "Methanol removal from organic mixtures by pervaporation using polypyrrole membranes," Journal of Membrane Science, 1996, vol. 117, pp. 303-309, Elsevier Science B.V.

* cited by examiner

*Primary Examiner* — Chester Barry
(74) *Attorney, Agent, or Firm* — Capitol City TechLaw, PLLC

(57) ABSTRACT

A method for yielding concentrated ethanol from an ethanol water solution yielded from ethanol fermentation of a water solution of saccharide generated by a saccharification of the lignocellulose by enzyme is provided. Water is separated from the ethanol water solution yielded from ethanol fermentation of the water solution of saccharide generated by the saccharification of the lignocellulose by enzyme with pervaporation method using a water separation membrane. Condensate prepared by condensing ethanol vapor existing in a space above a liquid level of the ethanol water solution is collected.

22 Claims, 2 Drawing Sheets

ETHANOL WATER SOLUTION CONCENTRATING METHOD

This application claims the foreign priority benefit under 35 U.S.C. §119 of Japanese Patent Application No. 2009-091493 filed on Apr. 3, 2009, the disclosure of which is incorporated herein by reference.

BACKGROUND OF THE INVENTION

1. Field of the Invention

The present invention relates to a method of yielding concentrated ethanol from an ethanol water solution yielded from ethanol fermentation of a saccharide water solution generated by saccharification of biomass containing lignocellulose by enzyme.

2. Description of the Related Art

In recent years, from the viewpoint of preventing global warming, it has been called on to reduce emission amount of carbon dioxide which is considered to be one of the reasons of global warming. Therefore, there has been considered to use a mixed fuel of ethanol and a liquid hydrocarbon compound such as gasoline as a vehicle fuel.

The ethanol can be yielded from fermentation of a plant material, for example, an agricultural crop such as sugar cane, corn or the like. Since the plant itself, the raw material of the plant material, has absorbed carbon dioxide via photosynthesis, even though the ethanol produced from the plant material is combusted, the emission amount of carbon dioxide is equal to the amount of carbon dioxide absorbed by the plant itself. In other words, the summed emission amount of carbon dioxide can be made theoretically equal to zero, which is the so-called carbon neutral effect.

However, if sugar cane, corn and the like are consumed in a large amount as the raw materials for preparing ethanol, there is a problem that the amount thereof supplied as food would be decreased. In this regard, there has been considered a technology to produce ethanol by using an inedible biomass containing lignocellulose as a substituent to the plant material such as sugar cane, corn or the like. As examples of the biomass containing lignocellulose, wood, rice straw, haulm, bamboo, pulp and waste materials originated therefrom, such as waste paper, may be given.

As a production method for ethanol, there has bee known a method as disclosed in Japanese Patent Laid-Open No. 2006-136263, Japanese Patent Laid-Open No. 2006-88136, in which biomass containing lignocellulose is saccharifized by enzyme by adding diastatic enzyme thereto so as to generate saccharide aqueous solution, and further the saccharide aqueous solution is added with ethanol fermentative bacteria to carry out ethanol fermentation, so as to yield ethanol water solution.

However, the ethanol water solution yielded from the above-mentioned ethanol production method is dilute, since the concentration of ethanol is ranged from 0.5 to 5.0 wt %. Therefore, there is a problem that it is difficult to use the same for automotive fuel as it is. Therefore, it is conceivable to yield concentrated ethanol by separating water from the ethanol water solution with pervaporation method using water separation membrane.

However, in the ethanol water solution concentrating method mentioned above, there is a disadvantage that the concentrated ethanol is still dilute at 3.0 to 5.5 wt %, even after separating a part of water from the ethanol water solution.

SUMMARY OF THE INVENTION

In view of such circumstances, an object of the present invention is to provide a method for yielding concentrated ethanol from an ethanol water solution yielded from ethanol fermentation of a water solution of saccharide generated by a saccharification of a lignocellulose by enzyme.

In order to achieve the object, the present inventors have given thorough consideration as to the reason why it is not possible to yield concentrated ethanol from the ethanol water solution yielded from ethanol fermentation of the water solution of saccharide generated by the saccharification of the lignocellulose by enzyme by the above-mentioned ethanol water solution concentrating method. As a result the present inventors have found that ethanol vapor evaporated from the ethanol water solution from which a part of water is separated therefrom resides in a space above the liquid level of the ethanol water solution.

The present inventors continued giving consideration on the basis of such findings, and have found that it is possible to yield concentrated ethanol by condensing the ethanol vapor residing in the space above the liquid level of the ethanol water solution, and attained the present invention.

In order to achieve the above object, the present invention provides a method of yielding concentrated ethanol from an ethanol water solution yielded from ethanol fermentation of a water solution of saccharide generated by a saccharification of a lignocellulose by enzyme, wherein: water is separated from the ethanol water solution with pervaporation method using a water separation membrane, and condensate prepared by condensing ethanol vapor present in a space above a liquid level of the ethanol water solution is collected.

In the method of the present invention, the pervaporation method is performed using the water separation membrane to the ethanol water solution yielded from ethanol fermentation of the water solution of saccharide generated by the saccharification of the lignocellulose by enzyme, so as to separate a part of water from the ethanol water solution.

On the other hand, the ethanol water solution performed with the pervaporation method has higher ethanol concentration compared to the ethanol water solution before being performed with the pervaporation method, because a part of water is separated therefrom. Therefore, ethanol is easier to evaporate from the ethanol water solution performed with pervaporation method. As a result, ethanol vapor resides in the space above the liquid level of the ethanol water solution performed with the pervaporation method.

In the method of the present invention, the ethanol vapor is condensed, and the yielded condensate is collected. The condensate prepared by condensing the ethanol vapor has higher ethanol concentration compared to the ethanol water solution before being performed with the pervaporation method.

Therefore, according to the method of the present invention, it becomes possible to yield concentrated ethanol from the ethanol water solution yielded from ethanol fermentation of the water solution of saccharide generated by the saccharification of the lignocellulose by enzyme.

Further, in the method of the present invention, a membrane composed of zeolite may be used as the water separation membrane. However, in the pervaporation method using the water solution membrane composed of zeolite, there is a problem that water separation performance of the water separation membrane is deteriorated from organic acid contained in the ethanol water solution yielded from ethanol fermentation of the water solution of saccharide generated by the saccharification of the lignocellulose by enzyme. In this case, it is necessary to adjust pH of the ethanol water solution before performing the pervaporation method, in order to prevent the water separation performance from being deteriorated by the organic acid.

Therefore, in the method of the present invention, as the water separating membrane, a membrane composed of polypyrrole doped with aromatic sulfonated ion or aliphatic sulfonated ion is preferably used in place of membrane composed of zeolite. In the method of the present invention in which the pervaporation method is carried out using the water separation membrane composed of polypyrrole, the water separation performance is not deteriorated by the organic acid, so that it becomes possible to directly yield concentrated ethanol from the ethanol water solution yielded from ethanol fermentation of the water solution of saccharide generated by the saccharification of the lignocellulose by enzyme without adjusting pH thereof.

Further, in the method of the present invention, it is preferable to reflux the condensate to the ethanol water solution. By doing so, the ethanol water solution performed with the pervaporation method has higher ethanol concentration, by being mixed with the condensate. As such, the amount of evaporation of the ethanol from the ethanol water solution performed with the pervaporation method is increased, and at the same time, the ethanol concentration of the ethanol vapor residing in the space above the liquid level of the ethanol water solution is increased.

By condensing the ethanol vapor with increased ethanol concentration as a result thereof, it becomes possible to yield condensate with higher ethanol concentration. Therefore, according to the method of the present invention in which the condensate is refluxed to the ethanol water solution, it becomes possible to yield ethanol concentrated to high concentration from the ethanol water solution yielded from ethanol fermentation of the water solution of saccharide generated by the saccharification of the lignocellulose by enzyme.

Further, in the method of the present invention, it is preferable to stir the ethanol water solution. By doing so, it is possible to prevent lignin or the organic acid contained in the ethanol water solution yielded from ethanol fermentation of the water solution of saccharide generated by the saccharification of the lignocellulose by enzyme from accumulating on the surface of the water separation membrane, and to promote water separation by the water separation membrane. As such, the ethanol water solution performed with the pervaporation method has higher ethanol concentration, so that the amount of evaporation of the ethanol from the ethanol water solution is increased, and at the same time, the ethanol concentration of the ethanol vapor residing in the space above the liquid level of the ethanol water solution is increased.

By condensing the ethanol vapor with increased ethanol concentration as a result thereof, it becomes possible to yield condensate with higher ethanol concentration. Therefore, according to the method of the present invention in which the ethanol water solution is stirred, it becomes possible to yield ethanol concentrated to higher concentration from the ethanol water solution yielded from ethanol fermentation of the water solution of saccharide generated by the saccharification of the lignocellulose by enzyme.

Further, in the method of the present invention, it is preferable to detect ethanol concentration of the condensate, and collect the condensate in accordance with the detected ethanol concentration. By doing so, it becomes possible to surely yield the ethanol concentrated to a desired concentration.

DETAILED DESCRIPTION OF THE PREFERRED EMBODIMENTS

Figure 1:
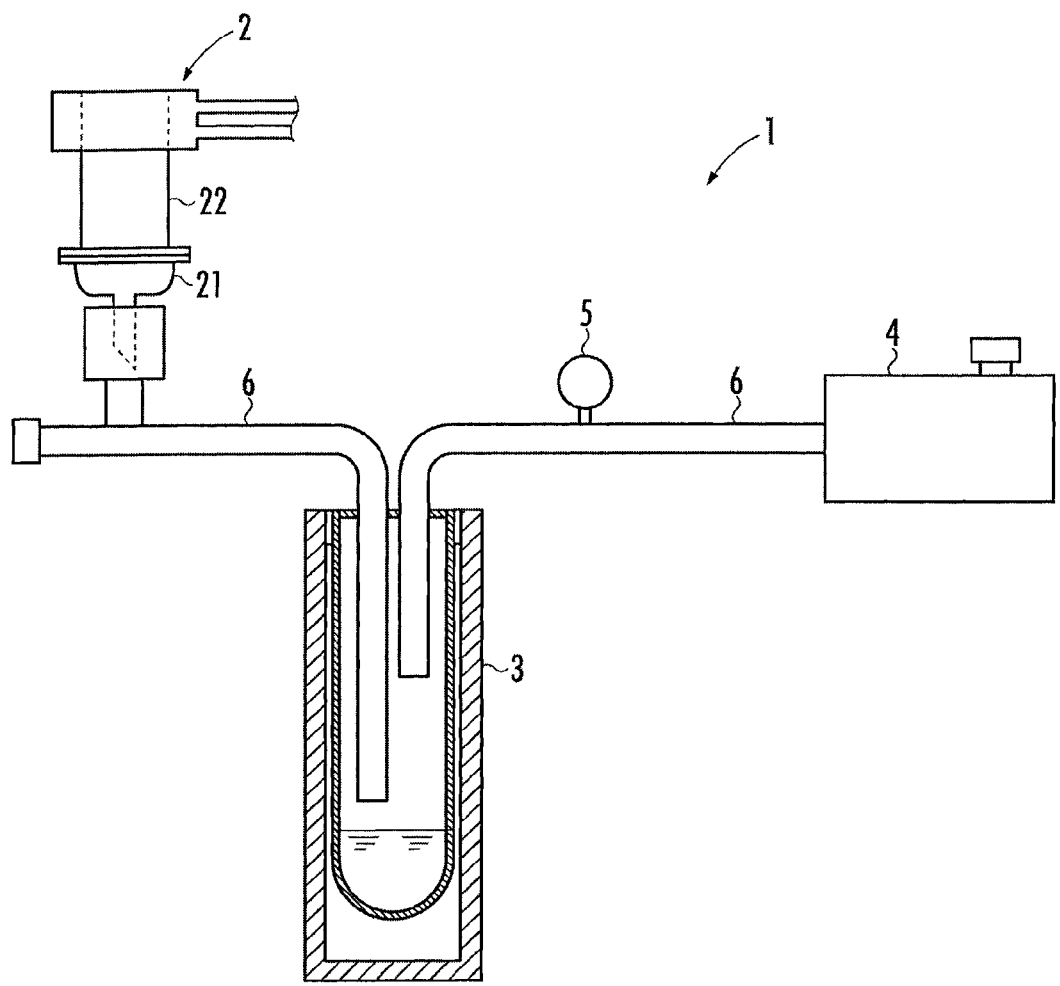
FIG. 1 is an explanatory view of overall pervaporation device performing an ethanol water solution concentrating method of the present embodiment.

An embodiment of the present invention will be now described in further detail with reference to the accompanying drawings. An ethanol water solution concentrating method of the present embodiment may be implemented, for example, by a pervaporation device 1 shown in FIG. 1.

The pervaporation device 1 is equipped with a pervaporation cell 2, a cold trap 3 containing liquid nitrogen, a vacuum pump 4, and a vacuum indicator 5. A conduit 6 is connected to the lower end of the pervaporation cell 2. The conduit 6 is connected to the vacuum pump 4 via the cold trap 3, and the vacuum indicator 5 is provided between the cold trap 3 and the vacuum pump 4.

Figure 2:
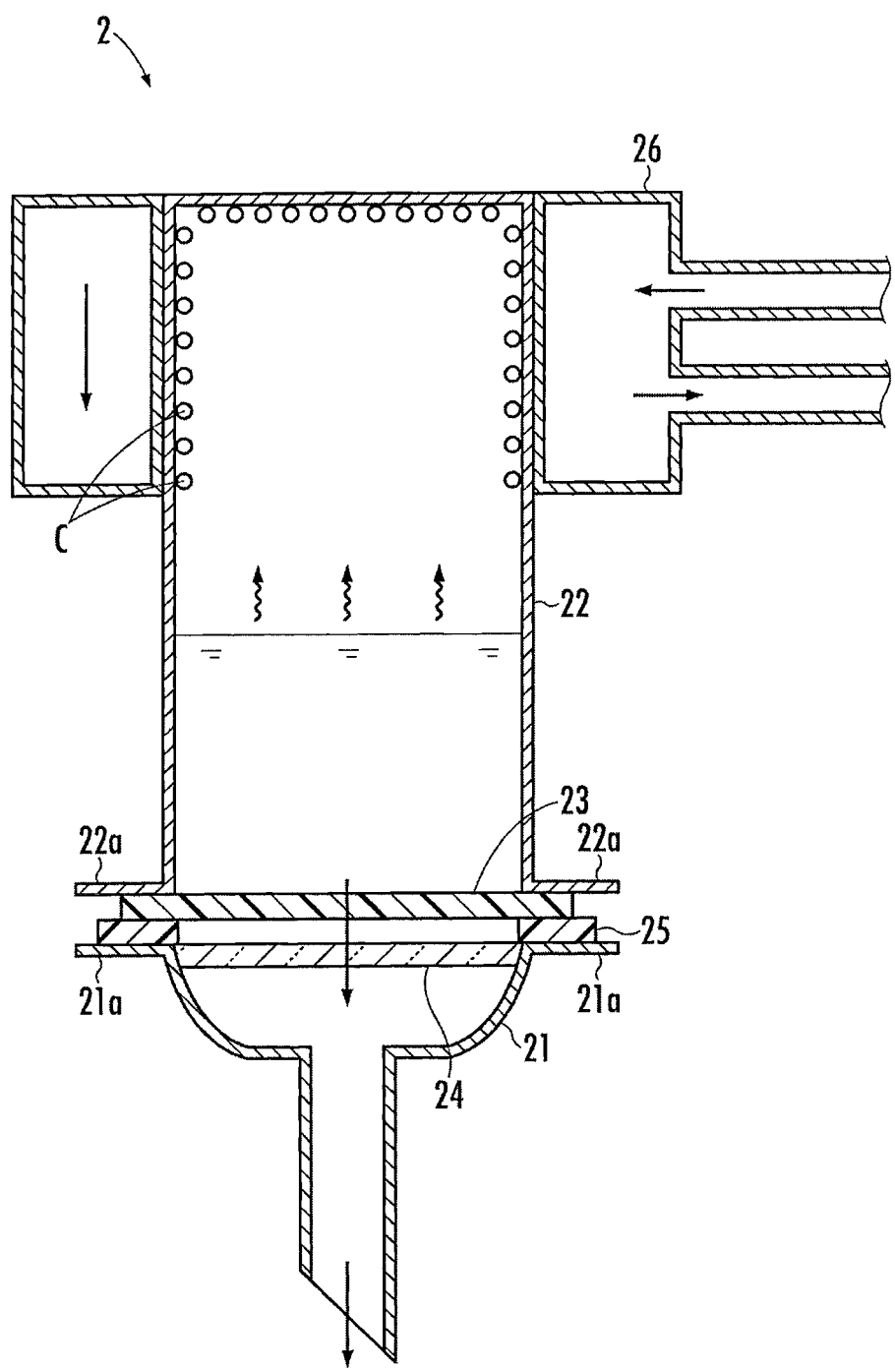
FIG. 2 is an explanatory cross-sectional view indicating an enlarged substantial part of the pervaporation device shown in FIG. 1.

As shown in FIG. 2, the pervaporation cell 2 is equipped with a depressurizing unit 21 connected to the conduit 6, an ethanol water solution storing unit 22 provided to the upper end side of the depressurizing unit 21, and a water separation membrane 23 provided between the depressurizing unit 21 and the ethanol water solution storing unit 22.

The depressurizing unit 21 takes an overall funnel shape. The depressurizing unit 21 is equipped at the upper end with a circular sintered glass filter (ADVANTEC Ltd., product name: KG-25) 24, and is also equipped at the outer circumference surface of the upper end with a flange 21a. The sintered glass filter 24 has an effective permeation area of 34.6 mm$^2$ (diameter 21 mm).

A sealing member 25 comprised of Parafilm (registered trademark, Alcan Packaging) is provided to the outer circumferential portion of the upper surface side of the sintered glass filter 24. The sealing member 25 is of an annular shape with the outer diameter of 28 mm, and inner diameter of 21 mm.

The circular water separation membrane 23 with a diameter of 26 mm is provided to the upper surface side of the sealing member 25. As the water separation membrane 23, a membrane composed of polypyrrole doped with aromatic sulfonated ion or with aliphatic sulfonated ion may preferably be used.

As examples of the aromatic sulfonated ion to be doped to polypyrrole, the following substances of chemical formulas (1) to (10) may be given.

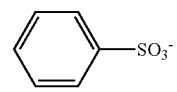

(1)

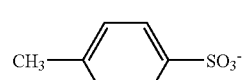

(2)

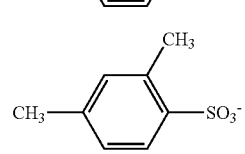

(3)

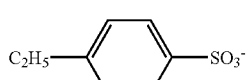

(4)

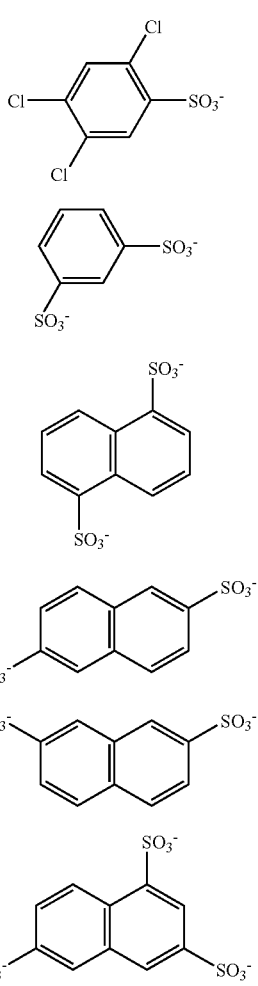

Further, as examples of the aliphatic sulfonated ion to be doped to polypyrrole, the following substances of chemical formulas (11) and (12), respectively, may be given.

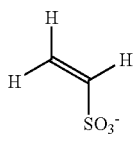

(11)

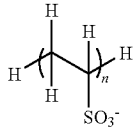

(12)

The water separation membrane 23 used in the present embodiment may be a membrane composed of polypyrrole doped with polyvinyl sulfonated ion, for example.

The ethanol water solution storing unit 22 provided to the upper surface side of the water separation membrane 23 has an inner diameter of 21 mm and height of 80 mm, and has a tubular body in which lower end thereof is opened and the upper end thereof is closed. The ethanol water solution storing unit 22 is equipped at the outer peripheral surface of the lower end with a flange 22a. An inner circumferential side at the lower side of the ethanol water solution storing unit 22 is exposed with the water separation membrane 23.

Further, a cooling unit 26 is attached to an outer circumferential surface at the upper side of the ethanol water solution storing unit 22. The cooling unit 26 cools the outer circumferential surface of the upper side of the ethanol water solution storing unit 22, by circulating cooling medium such as water and liquid nitrogen therein.

Next, the ethanol water solution concentrating method of the present embodiment will be explained with reference to FIGS. 1 and 2. First, the ethanol water solution yielded from ethanol fermentation of the water solution of saccharide generated by the saccharification of the lignocellulose by enzyme is supplied to the ethanol water solution storing unit 22. At this time, in the ethanol water solution storing unit 22, the liquid level of the ethanol water solution stored therein is made to be positioned below the lower end of the cooling unit 26.

Next, by activating the vacuum pump 4, the depressurizing unit 21 is depressurized via the conduit 6. By doing so, pervaporation method is performed to the ethanol water solution stored in the ethanol water solution storing unit 22, and a part of water is separated from the ethanol water solution. The separated water turns into water vapor by permeating through the water separation membrane 23, which is introduced into the cold trap 3 via the depressurizing unit 21 and the conduit 6, and is condensed.

The water separation membrane 23 mainly permeates water contained in the ethanol water solution. However, it also permeates a fraction of ethanol contained in the ethanol water solution. Therefore, a part of the water separated from the ethanol water solution is substantially an ethanol water solution having extremely low ethanol concentration than the ethanol water solution.

On the other hand, the ethanol water solution performed with the pervaporation method has higher ethanol concentration compared to the ethanol water solution before being performed with the pervaporation method, by separating a part of water as the substantial ethanol water solution having extremely low ethanol concentration. As such, ethanol is made easier to evaporate from the ethanol water solution performed with the pervaporation method. As a result, ethanol vapor resides in a space above the liquid level of the ethanol water solution performed with the pervaporation method.

Next, the cooling medium is made to circulate inside the cooling unit 26, so as to cool the upper portion of the ethanol water solution storing unit 22. By doing so, the ethanol vapor residing in the upper portion of the ethanol water solution storing unit 22 is condensed, and is attached to the inner circumferential surface at the upper portion of the ethanol water solution storing unit 22 as a condensate C.

The ethanol vapor contains water vapor evaporated from the ethanol water solution, but the volume thereof is small compared to the ethanol vapor. Therefore, the condensate C which is yielded by condensing the ethanol vapor is an ethanol water solution in which ethanol is dissolved in water, but the ethanol concentration thereof is higher compared to the ethanol water solution before being performed with the pervaporation method.

Therefore, by collecting the condensate C attached to the inner circumferential surface at the upper portion of the ethanol water solution storing unit 22 with a collecting means not shown, the concentrated ethanol may be yielded from the ethanol water solution yielded from ethanol fermentation of the water solution of saccharide generated by the saccharification of the lignocellulose by enzyme.

Further, in the ethanol water solution concentrating method of the present embodiment, the pervaporation method is performed using the membrane composed of polypyrrole doped with aromatic sulfonated ion or with aliphatic sulfonated ion as the water separation membrane 23. With such water separation membrane 23, upon performing the pervaporation method, water separation performance is not deteriorated because of the organic acid contained in the ethanol water solution yielded from ethanol fermentation of the water solution of saccharide generated by the saccharification of the lignocellulose by enzyme. Therefore, in the ethanol water solution concentrating method of the present embodiment, concentrated ethanol may be directly yielded from the ethanol water solution, without pH adjustment.

Further, in the ethanol water solution concentrating method of the present embodiment, it is preferable to reflux the condensate C to the ethanol water solution. The reflux may be carried out by, for example, strongly cooling the upper portion of the ethanol water solution storing unit 22 with the cooling unit 26, make the condensate C attached to the inner circumference surface of the upper portion thereof combine with one another so as to enlarge the droplet diameter, and let the condensate C drop into the ethanol water solution stored in the ethanol water solution storing unit 22.

When the condensate C is refluxed to the ethanol water solution, the ethanol concentration of the ethanol water solution performed with the pervaporation method is increased by being mixed with the condensate C. By doing so, the amount of evaporation of the ethanol from the ethanol water solution performed with the pervaporation method is increased, and at the same time, the ethanol concentration of the ethanol vapor residing in the space above the liquid level of the ethanol water solution is increased.

As a result, by condensing the ethanol vapor with higher ethanol concentration, it becomes possible to yield the condensate C with higher ethanol concentration. Therefore, with the method of the present embodiment in which the condensate C is refluxed to the ethanol water solution, it becomes possible to yield the condensed ethanol to high concentration from the ethanol water solution yielded from ethanol fermentation of the water solution of saccharide generated by the saccharification of the lignocellulose by enzyme.

Further, in the ethanol water solution concentrating method of the present embodiment, it is preferable to stir the ethanol water solution stored in the ethanol water solution storing unit 22. The stirring may be carried out, for example, with a stirring means not shown such as a magnetic stirrer, a mechanical stirrer and the like.

With such construction, it becomes possible to prevent lignin or the organic acid contained in the ethanol water solution yielded from ethanol fermentation of the water solution of saccharide generated by the saccharification of the lignocellulose by enzyme from accumulating on the surface of the water separation membrane 23, and to promote water separation by the water separation membrane 23. By doing so, ethanol concentration of the ethanol water solution performed with the pervaporation method is increased, so that the amount of evaporation of the ethanol from the ethanol water solution is increased, and at the same time, the ethanol concentration of the ethanol vapor residing in the space above the liquid level of the ethanol water solution is increased.

As a result, by condensing the ethanol vapor with higher ethanol concentration, it becomes possible to yield the condensate C with higher ethanol concentration. Therefore, with the method of the present embodiment in which the ethanol water solution is stirred, it becomes possible to yield the condensed ethanol with higher concentration from the ethanol water solution yielded from ethanol fermentation of the water solution of saccharide generated by the saccharification of the lignocellulose by enzyme.

Still further, in the ethanol water solution concentrating method of the present embodiment, it is preferable to detect the ethanol concentration of the condensate C, and to collect the condensate C in accordance with the detected ethanol concentration. The detection of the ethanol concentration may be carried out, for example, by measuring the collected condensate C with a gas chromatograph not shown. By doing so, it becomes possible to surely yield the ethanol concentrated to a desired concentration.

Next, examples of the present invention will be explained.

EXAMPLE 1

In the present example, first, the ethanol water solution yielded from ethanol fermentation of the water solution of saccharide generated by the saccharification of the lignocellulose by enzyme is prepared. The preparation is carried out as follows.

First, naturally dried rice straws are pulverized with a cutting mill, so as to yield rice straw chips. Next, 20 kg of yielded rice straw chips are subjected to thermal treatment by water vapor, by maintaining the rice straw chips in a high-pressure boiler under water vapor atmosphere at a temperature of 180° C. for 30 minutes.

Next, a commercially available diastatic enzyme (commercial name: GC220 manufactured by Genencor Kyowa Co. Ltd., a mixture of cellulose, hemicellulase and the like) is introduced at a ratio of 10 wt % with respect to the dried weight of the rice straw chips subjected to thermal treatment by the water vapor. Moreover, to the rice straw chips added with the diastatic enzyme, acetate buffer and ion-exchanged water are added to make the pH thereof at 4.5. The acetate buffer and the ion-exchanged water are added to adjust the aqueous solution in such a manner that the dried weight of the rice straw chips after heat treatment with respect to 1 L of the yielded aqueous solution is 20% (w/v).

Thereafter, the prepared aqueous solution is introduced into a mush tun, maintained at a temperature of 50° C. for 24 hours while stirring, and saccharification with diastatic enzyme is performed to lignocellulose contained in the prepared aqueous solution, so as to yield an enzyme-treated solution including saccharide (saccharide aqueous solution). Next, the yielded enzyme-treated solution is separated into solid and liquid using a filter press, and then ultrafiltered to remove the diastatic enzyme therefrom, so as to yield the saccharide aqueous solution from which the diastatic enzyme is removed.

Next, the saccharide aqueous solution from which the diastatic enzyme is removed is introduced into a fermentor, and is added with ethanol fermentative bacteria (Saccharomyces cerevisiae; yeast S288C (NBRC 1136)) so that the same becomes 2 wt % in wet weight. Then, the saccharide aqueous solution added with the ethanol fermentative bacteria is maintained at a temperature of 30° C. for 6 to 8 hours while stirring, so as to ferment the saccharide into ethanol and yield an ethanol fermentation solution.

Thereafter, the ethanol fermentative bacteria is removed by ultrafiltering the yielded ethanol fermentation solution, so as to yield the ethanol water solution. With the above-explained process, the ethanol water solution yielded from ethanol fermentation of the water solution of saccharide generated by the saccharification of the lignocellulose by enzyme is prepared.

Next, upon measuring the ethanol concentration of the yielded ethanol water solution with gas chromatograph, the ethanol concentration was 0.89 wt %.

Then, 13.3 g of the yielded ethanol water solution is supplied to the ethanol water solution storing unit 22 of the pervaporation device 1 shown in FIG. 1. Next, by activating the vacuum pump 4, the depressurizing unit 21 is depressurized via the conduit 6. The pressure inside the conduit 6 measured by the vacuum indicator 5 was 500 Pa. Hence, the pervaporation method is performed to the ethanol water solution stored in the ethanol water solution storing unit 22.

During the pervaporation, the ethanol water solution is stirred with the magnetic stirrer, and water at a temperature of 0° C. is circulated inside the cooling unit 26. Further, as the water separation membrane 23, a membrane composed of polypyrrole doped with polyvinyl sulfonated ion is used.

With the pervaporation method, water is separated from the ethanol water solution stored in the ethanol water solution storing unit 22, and at the same time, ethanol vapor is evaporated therefrom. The separated water turns into water vapor by permeating through the water separation membrane 23, which is then stored in the cold trap 3 via the depressurizing unit 21 and the conduit 6.

On the other hand, the ethanol vapor residing in the space above the liquid level of the ethanol water solution performed with the pervaporation method turns into the condensate C by being cooled by the cooling unit 26, which is then attached to the inner circumferential surface at the upper portion of the ethanol water solution storing unit 22. Further, the condensate C attached to the inner circumferential surface at the upper portion of the ethanol water solution storing unit 22 is cooled further, and is dropped to the ethanol water solution stored in the ethanol water solution storing unit 22.

After performing the pervaporation method for 69 hours, the condensate C attached to the inner circumferential surface at the upper portion of the ethanol water solution storing unit 22 is collected by a dropper. Then, the ethanol concentration of the yielded condensate C is measured by the gas chromatograph, which turned out to be 74 wt %.

Therefore, according to the ethanol water solution concentrating method of the present embodiment, it is apparent that, from the ethanol water solution yielded from ethanol fermentation of the saccharide aqueous solution generated by the saccharification of the lignocellulose by enzyme in which ethanol concentration is 0.89 wt %, ethanol concentrated to 74 wt % may be yielded.

What is claimed is:

1. An ethanol water solution concentrating method of yielding concentrated ethanol from a liquid phase ethanol water solution produced from ethanol fermentation of a water solution of saccharide generated by a saccharification of a lignocellulose by enzyme, comprising
    separating water from the liquid phase ethanol water solution by prevaporation using a water separation membrane;
    condensing ethanol vapor present in a space above a liquid level of the liquid phase ethanol water solution to form a condensate; and
    collecting the condensate,
    wherein the condensate comprises concentrated ethanol.

2. The ethanol water solution concentrating method according to claim 1, wherein the water separating membrane comprises polypyrrole doped with aromatic sulfonated ion.

3. The ethanol water solution concentrating method according to claim 1, wherein the water separating membrane comprises polypyrrole doped with aliphatic sulfonated ion.

4. The ethanol water solution concentrating method according to claim 3 wherein the aliphatic sulfonated ion comprises polyvinyl sulfonated ion.

5. The ethanol water solution concentrating method according to claim 1, wherein condensation of the ethanol vapor is performed by circulating a cooling medium to a cooling unit provided to the space above the liquid level of the liquid phase ethanol water solution.

6. The ethanol water solution concentrating method according to claim 5, wherein the cooling medium comprises water.

7. The ethanol water solution concentrating method according to claim 5, wherein the cooling medium comprises liquid nitrogen.

8. The ethanol water solution concentrating method according to claim 1, wherein the condensate is refluxed to the liquid phase ethanol water solution.

9. The ethanol water solution concentrating method according to claim 1, further comprising stirring the liquid phase ethanol water solution.

10. The ethanol water solution concentrating method according to claim 9, wherein the stirring is performed with a magnetic stirrer.

11. The ethanol water solution concentrating method according to claim 9, wherein the stirring is performed with a mechanical stirrer.

12. The ethanol water solution concentrating method according to claim 1, further comprising
    detecting the ethanol concentration of the condensate, and
    collecting the condensate in accordance with the detected ethanol concentration.

13. The ethanol water solution concentrating method according to claim 12, wherein the ethanol concentration of the condensate is detected by gas chromatography.

14. An ethanol water solution concentrating method comprising
    providing a liquid phase ethanol water solution produced from ethanol fermentation of a water solution of saccharide generated by a saccharification of a lignocellulose by enzyme;
    separating water from the liquid phase ethanol water solution by prevaporation using a water separation membrane;
    condensing ethanol vapor present in a space above a liquid level of the liquid phase ethanol water solution to form a condensate; and
    collecting the condensate,
    wherein the condensate comprises concentrated ethanol.

15. The ethanol water solution concentrating method according to claim 14, wherein the water separating membrane comprises polypyrrole doped with aromatic sulfonated ion.

16. The ethanol water solution concentrating method according to claim 14, wherein the water separating membrane comprises polypyrrole doped with aliphatic sulfonated ion.

17. The ethanol water solution concentrating method according to claim 16 wherein the aliphatic sulfonated ion comprises polyvinyl sulfonated ion.

18. The ethanol water solution concentrating method according to claim 14, wherein condensation of the ethanol vapor is performed by circulating a cooling medium to a cooling unit provided to the space above the liquid level of the liquid phase ethanol water solution.

19. The ethanol water solution concentrating method according to claim 14, wherein the condensate is refluxed to the liquid phase ethanol water solution.

20. The ethanol water solution concentrating method according to claim 14, further comprising stirring the liquid phase ethanol water solution.

21. The ethanol water solution concentrating method according to claim 14, further comprising
- detecting the ethanol concentration of the condensate; and
- collecting the condensate in accordance with the detected ethanol concentration.

22. An ethanol water solution concentrating method of yielding concentrated ethanol from a liquid phase ethanol water solution produced from ethanol fermentation of a water solution of saccharide generated by a saccharification of a lignocellulose by enzyme, comprising
- separating water from the liquid phase ethanol water solution by prevaporation using a water separation membrane;
- condensing ethanol vapor present in a space above a liquid level of the liquid phase ethanol water solution to form a condensate by circulating liquid nitrogen to a cooling unit provided to the space above the liquid level of the liquid phase ethanol water solution; and
- collecting the condensate,
- wherein the condensate comprises concentrated ethanol.

* * * * *